United States Patent
Georgakopoulos et al.

(10) Patent No.: US 10,918,865 B2
(45) Date of Patent: Feb. 16, 2021

(54) CAROTID SINUS NERVE STIMULATION

(71) Applicant: Barologics, Inc., Carver, MN (US)

(72) Inventors: Dimitrios Georgakopoulos, Plymouth, MN (US); Molly Wade, Carver, MN (US)

(73) Assignee: BAROLOGICS, INC., Carver, MN (US)

( * ) Notice: Subject to any disclaimer, the term of this patent is extended or adjusted under 35 U.S.C. 154(b) by 107 days.

(21) Appl. No.: 16/393,536

(22) Filed: Apr. 24, 2019

(65) Prior Publication Data
US 2019/0329037 A1    Oct. 31, 2019

Related U.S. Application Data

(60) Provisional application No. 62/662,600, filed on Apr. 25, 2018.

(51) Int. Cl.
*A61N 1/36* (2006.01)
*A61B 5/00* (2006.01)
(Continued)

(52) U.S. Cl.
CPC ........ *A61N 1/36053* (2013.01); *A61B 5/0006* (2013.01); *A61B 5/0205* (2013.01); *A61B 5/04085* (2013.01); *A61N 1/36057* (2013.01); *A61N 1/36117* (2013.01); *A61N 1/36135* (2013.01); *A61N 1/36157* (2013.01);
(Continued)

(58) Field of Classification Search
CPC ............ A61N 1/36053; A61N 1/36157; A61N 1/36171; A61N 1/36175; A61N 1/36178; A61N 1/0556; A61N 1/36057; A61N 1/36117; A61N 1/36135; A61B 5/0006;
(Continued)

(56) References Cited

U.S. PATENT DOCUMENTS

| 6,292,703 B1 | 9/2001 | Meier | |
| 2009/0275997 A1* | 11/2009 | Faltys | A61N 1/056 607/2 |

(Continued)

FOREIGN PATENT DOCUMENTS

| DE | 19847446 | 4/2000 |
| WO | WO1997018856 | 5/1997 |
| WO | WO20150108909 | 7/2015 |

OTHER PUBLICATIONS

International Search Report and Written Opinion for International Application No. PCT/US2019/028935, dated Sep. 11, 2019, 14 pages.

*Primary Examiner* — Amanda K Hulbert
*Assistant Examiner* — Natasha Patel
(74) *Attorney, Agent, or Firm* — Merchant & Gould P.C.

(57) ABSTRACT

A method for stimulating nerve fibers to treat a condition in a patient first involves identifying carotid sinus nerve afferent fibers in a first side of the patient's neck and identifying cardiac-specific vagal nerve afferent fibers in the first side of the patient's neck. The method further involves placing a first multipolar electrode device around the carotid sinus nerve afferent fibers and the cardiac-specific vagal nerve afferent fibers. Finally, the method involves stimulating the carotid sinus nerve afferent fibers and the cardiac-specific vagal nerve afferent fibers, using the first multipolar electrode device. This method may be performed on a second side of the neck as well.

19 Claims, 9 Drawing Sheets

(51) Int. Cl.
   *A61B 5/0205*   (2006.01)
   *A61B 5/0408*   (2006.01)
   *A61B 5/021*    (2006.01)
   *A61B 5/024*    (2006.01)

(52) U.S. Cl.
   CPC ..... *A61N 1/36171* (2013.01); *A61N 1/36175* (2013.01); *A61N 1/36178* (2013.01); *A61B 5/024* (2013.01); *A61B 5/02108* (2013.01)

(58) Field of Classification Search
   CPC .............. A61B 5/0205; A61B 5/04085; A61B 5/02108; A61B 5/024
   See application file for complete search history.

(56) References Cited

U.S. PATENT DOCUMENTS

| | | |
|---|---|---|
| 2013/0204328 A1 | 8/2013 | Stahmann |
| 2016/0250474 A1* | 9/2016 | Stack ................ A61N 1/36114 607/44 |
| 2018/0104491 A1* | 4/2018 | Lerner ................ A61M 1/1086 |

* cited by examiner

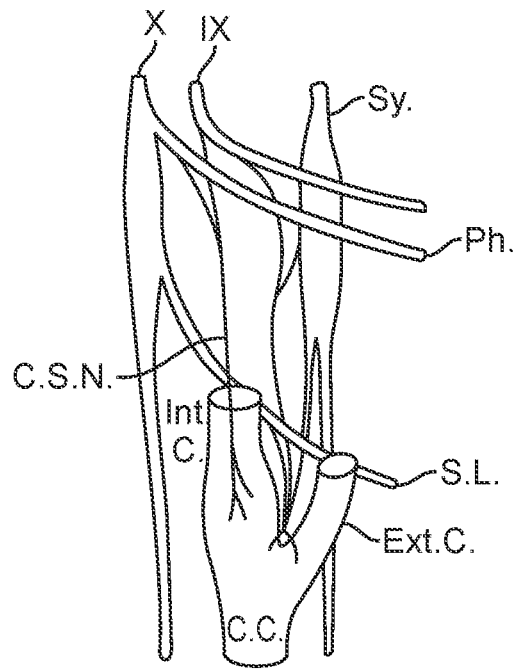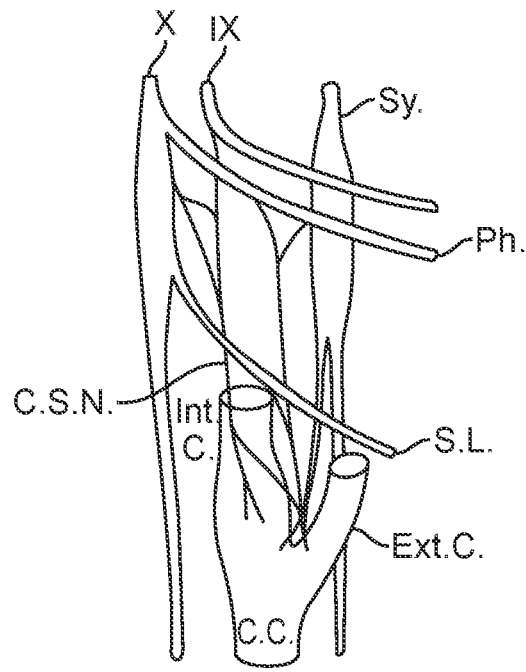
FIG. 3A            FIG. 3B
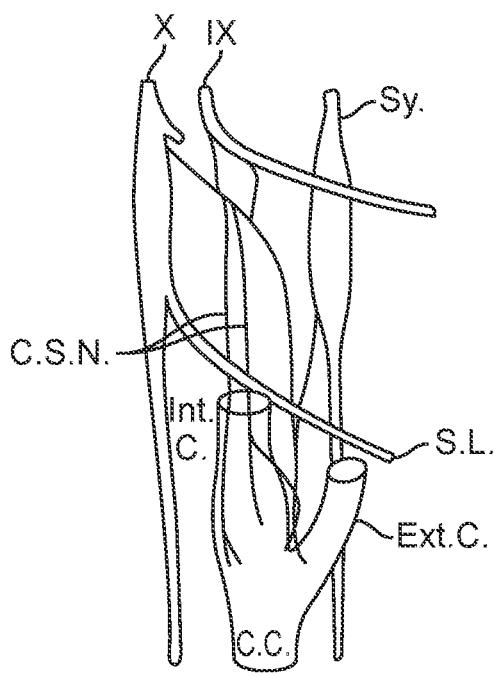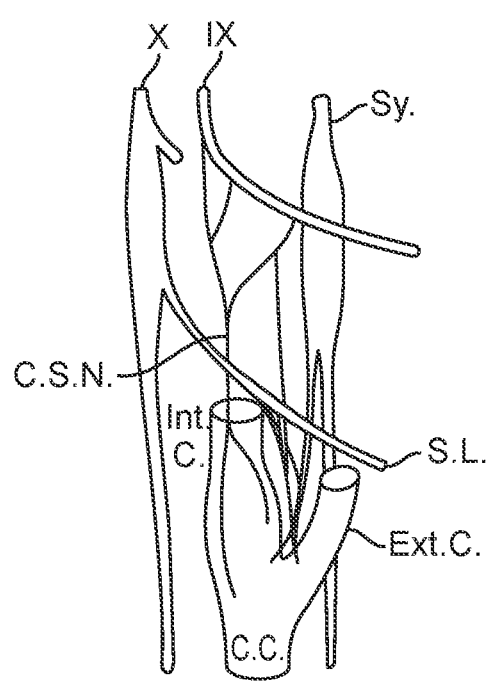
FIG. 3C            FIG. 3D

CAROTID SINUS NERVE STIMULATION

CROSS-REFERENCE TO RELATED APPLICATIONS

This application claims the benefit of U.S. Provisional Patent Application No. 62/662,600, filed Apr. 25, 2018, entitled, "Carotid Sinus Nerve Stimulation." The disclosure of this priority application is hereby incorporated by reference in its entirety into the present application.

TECHNICAL FIELD

This application is directed to medical devices, systems and methods. More specifically, the application is directed to devices, systems and methods for nerve stimulation to treat one or more cardiovascular disorders.

BACKGROUND OF THE INVENTION

Millions of patients worldwide suffer from cardiovascular diseases, such as hypertension (high blood pressure) and heart failure. Many different pharmaceutical and medical device treatments have been developed to treat hypertension and heart failure, in particular, but many of these treatments have been either completely ineffective or at least ineffective in large subsets of patients. For example, approximately one in ten people with high blood pressure are treatment resistant (in other words, pharmaceuticals do not help to reduce their blood pressure.) Approximately one hundred million people worldwide suffer from treatment resistant high blood pressure. These patients are three times more likely to suffer from a cardiovascular event, such as a heart attack, compared to patients who are able to control their high blood pressure with medications.

A number of different medical devices have been tried to treat drug resistant high blood pressure. One example is a procedure in which a catheter is threaded into the arteries leading to the kidneys, and radiofrequency energy is sent out of the catheter in an attempt to destroy the small nerves surrounding the arteries. Another example is an implantable stimulator for stimulating baroreceptors in the neck by applying energy to the wall of the carotid artery. Unfortunately, these device approaches have not been proven effective. Thus, hundreds of millions of patients suffer from currently-untreatable high blood pressure, which very often leads to serious cardiovascular consequences. Unfortunately, other serious health conditions, such as congestive heart failure and kidney failure, have similar stories.

Therefore, it would be desirable to have improved devices, systems and methods for hypertension, heart failure and/or other cardiovascular conditions. Ideally, such devices, systems and methods would be minimally invasive or less invasive and also effective at treating their target. At least some of these objectives are addressed in this application.

BRIEF DESCRIPTION OF THE DRAWINGS

FIGS. 3A-3D are anatomical drawings showing four different patterns of a vagus nerve in the area of the carotid sinus;

DETAILED DESCRIPTION OF THE INVENTION

This application describes methods, devices and systems for stimulating nerves to treat hypertension, coronary heart disease, heart failure, kidney disease and/or any of a number of other disease states in humans or animals. Although the following description will focus on the treatment of drug resistant hypertension (high blood pressure), the aspects and principles described below may be used to treat, or adapted for use to treat, any of a number of other cardiovascular or other conditions. Thus, despite the focus of the following description on one disease state, the scope of this application and the methods, devices and systems described herein is not limited to any one disease or condition.

Figure 2:
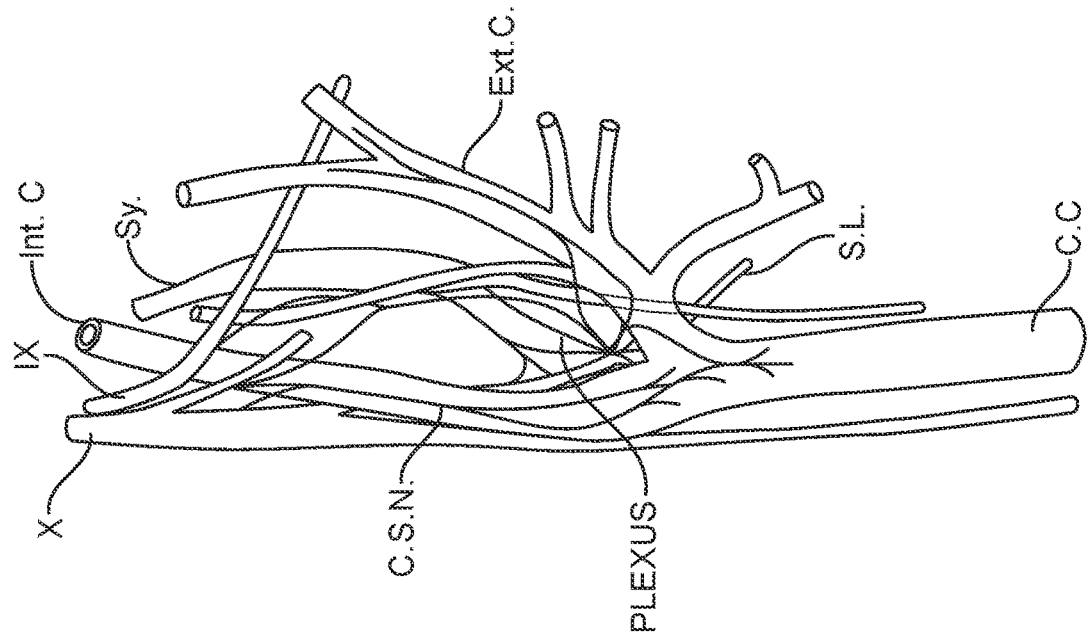
FIG. 2 is a different anatomical drawing of a carotid sinus and nerves in that anatomical area.
Figure 1:
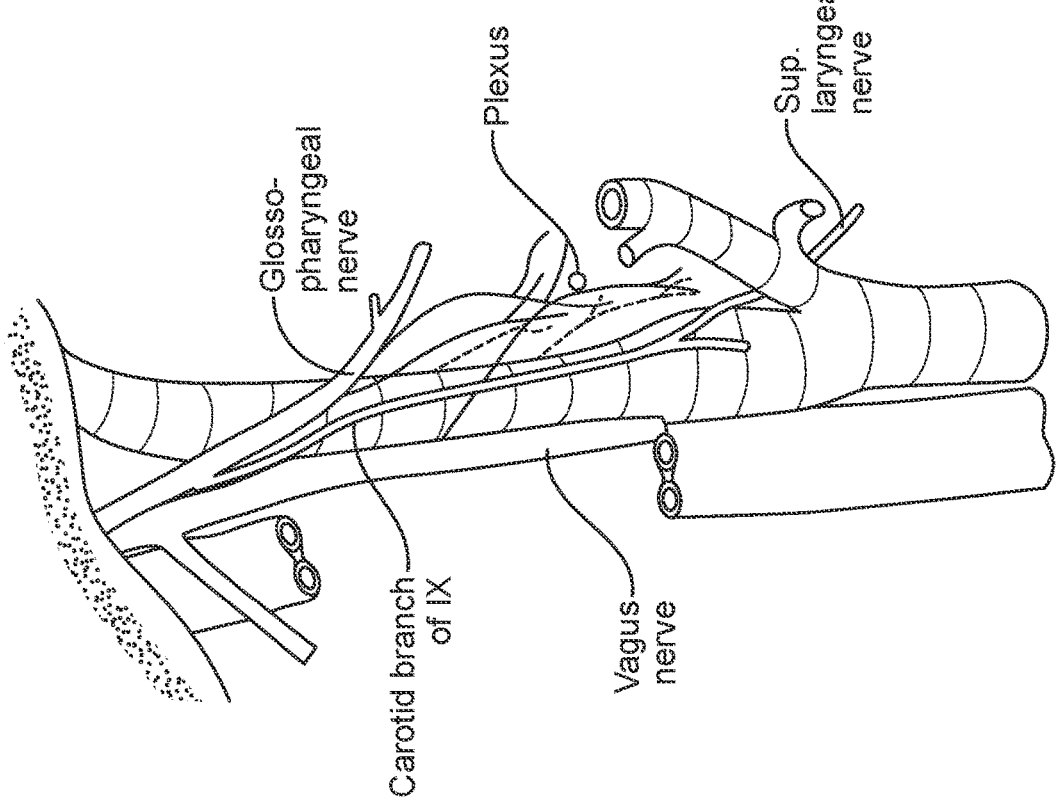
FIG. 1 is an anatomical drawing of a carotid sinus and nerves in that anatomical area.

Referring now to FIGS. 1 and 2, anatomical studies have shown that there are two branches of the carotid sinus nerve CSN, arising from its origin in the main trunk of the glossopharyngeal nerve IX (i.e., cranial nerve IX, labeled "IX" in FIG. 2). (The vagus nerve, or cranial nerve X, labeled "X" in FIG. 2.) One branch of the carotid sinus nerve courses along the anteromedial aspect of the internal carotid artery ("Int. C" in FIG. 2), terminating in the bifurcation of the carotid sinus and plexus lying posterior and medial to the internal carotid artery in the bifurcation of the common carotid artery ("CC in FIG. 2). The other branch terminates in the plexus directly.

Referring to FIGS. 3A-3D, in addition to the carotid sinus nerve CSN, the inter-carotid plexus contains afferent branches of the vagus nerve X, which are specific to the baroreflex. Four distinct patterns, illustrated in FIGS. 3A-3D, have been identified, and all contain branches of the vagus nerve X in the inter-carotid plexus.

The carotid sinus nerve CSN and the vagus nerve X both include afferent nerve fibers, which carry signals to the central nervous system, and efferent nerve fibers, which carry signals away from the central nervous system. In some embodiments, the devices, systems and methods described herein involve stimulating carotid sinus afferent nerve fibers and cardiac-specific vagal afferent nerve fibers, in order to treat hypertension and/or any other suitable condition. In some embodiments, one or both of these types of nerve fibers (carotid sinus afferent nerve fibers and/or cardiac-specific vagal afferent nerve fibers) may be identified before they are stimulated. For the purposes of this application, carotid sinus afferent nerve fibers may be generally referred to as "the carotid sinus nerve," and cardiac-specific vagal afferent nerve fibers may be generally referred to as "the vagus nerve." In some embodiments, for example, electrodes of the system described herein may be placed on, over or around the carotid sinus nerve and the vagus nerve, and such an electrode may be used to stimulate carotid sinus afferent nerve fibers and/or cardiac-specific vagal afferent nerve fibers.

Figure 4:
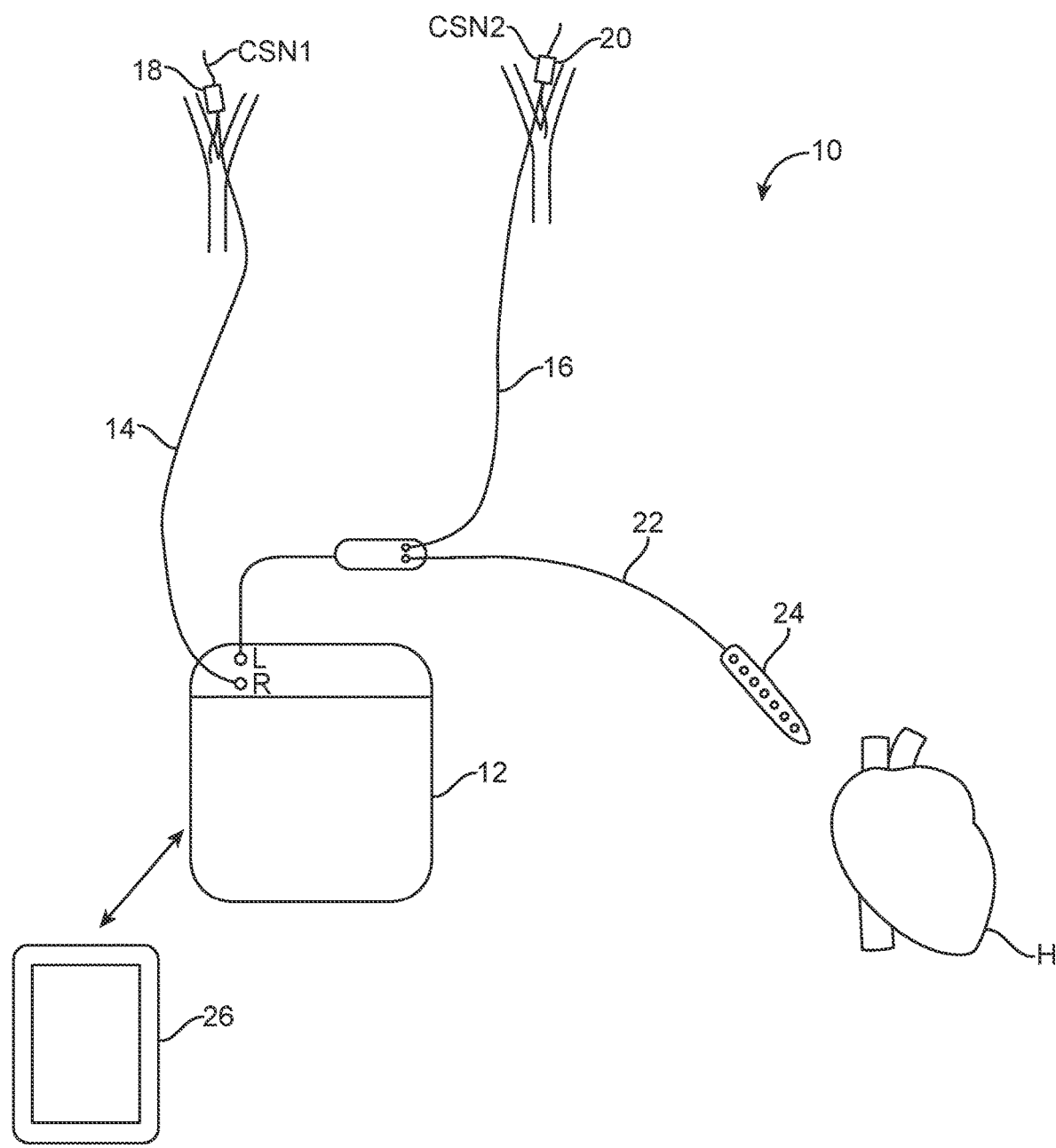
FIG. 4 is a diagrammatic representation of a system for stimulating a carotid sinus nerve, according to one embodiment.

Referring now to FIG. 4, one embodiment of an implantable carotid sinus nerve stimulation system 10 is illustrated. In this embodiment, the system 10 includes a pulse generator 12 (alternatively referred to as a "box" or "can"), a right lead 14 coupled with a right electrode device 18, a left lead 16 coupled with a left electrode device 20, a third lead 22 coupled with a subcutaneous electrocardiogram (ECG) sensor 24, and a computing device 26 wirelessly coupled with the pulse generator 12. In use, the pulse generator 12 is implanted subcutaneously in the upper chest region and holds the "brains" and battery of the implantable portion of the system 10. The leads 14, 16 connect to the pulse generator 12 and tunnel under the patient's skin to the electrode devices 16, 18 (also sometimes referred to simply as "electrodes"), which are placed bilaterally around the carotid sinus nerves and the vagus nerve. In an alternative embodiment, the system 10 may include only the right lead 14 and the right electrode device 18, or the left lead 16 and the left electrode device 20. The third lead 22 is also tunneled under the patient's skin and connects to the ECG sensor 24, which is placed subcutaneously near the patient's heart H. The ECG sensor 24 may, for example, include a paddle-shaped substrate with multiple electrodes attached to it.

The computing device 26 may be any suitable computing device, including but not limited to a smart tablet, smart phone, laptop computer, desktop computer, medical monitoring device or the like. The computing device 26 may transmit data to, and receive data from, the pulse generator 12 wirelessly, using Bluetooth wireless technology or any other wireless protocol. The pulse generator 12 may send data such as but not limited to ECG data sensed by the ECG sensor 24. The computing device 26 may be used to program stimulation parameters into the pulse generator 12 and/or to adjust such parameters. Any suitable information may be shared between the pulse generator 12 and the computing device 26. To ensure patient safety and privacy, a program on the computing device 26 and/or on the pulse generator 12 may include a lock, passkey, firewall and/or any other security measures to restrict access to the pulse generator 12 to only approved healthcare providers or other approved personnel.

Figure 5:
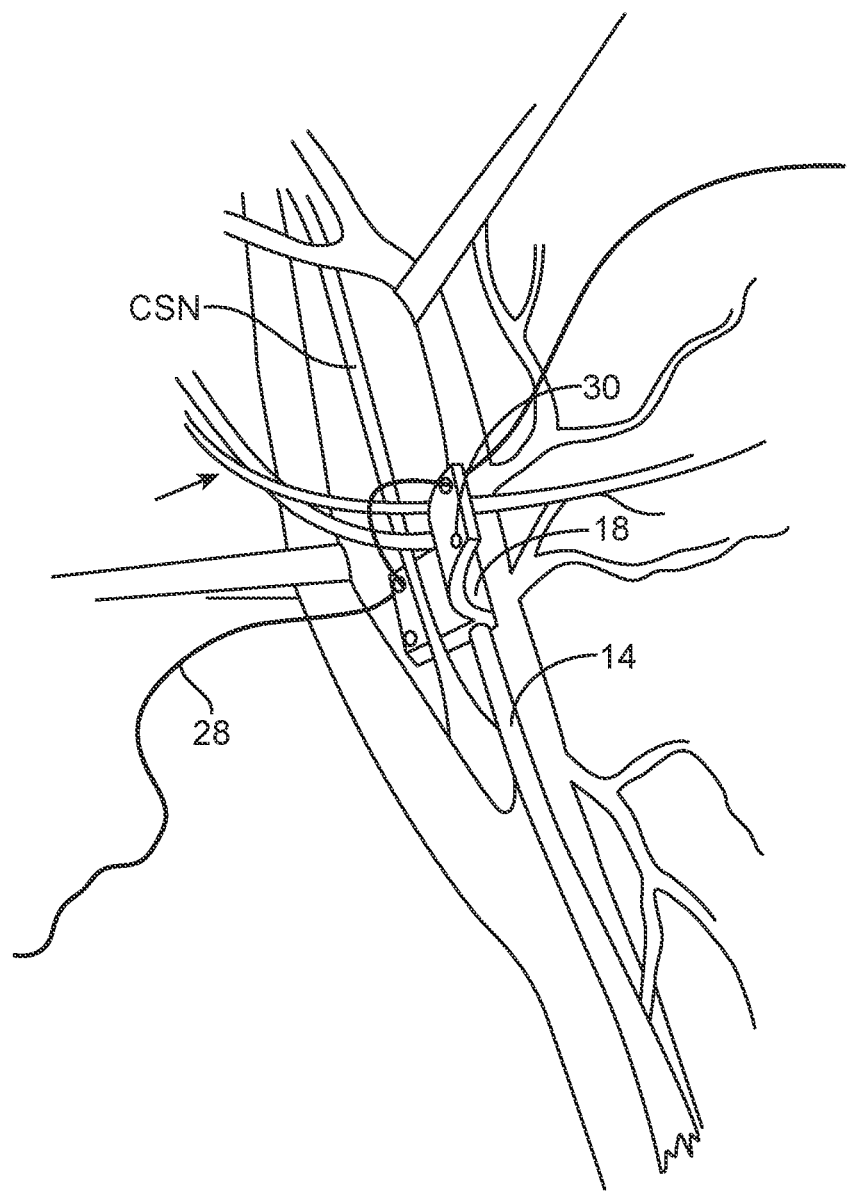
FIG. 5 is a perspective view of a system for stimulating a carotid sinus nerve, showing a multipolar electrode being placed around a carotid sinus nerve, according to one embodiment.

Referring now to FIG. 5, one embodiment of the electrode device 18 is shown being placed over a carotid sinus nerve CSN. In general, the electrode device 18 may be placed over the plexus of nerves that includes the carotid sinus nerve CSN and the vagus nerve, as described above in reference to the anatomical drawings in FIGS. 1-3D. In this embodiment, the electrode device 18 is book shaped, in that it is connected along one edge and open along an opposite edge. The open edge may be turned open, to envelop or surround one or more nerves, and then closed to hold the nerve(s). In various embodiments, any suitable closure mechanism may be used, for closing the open end of the "book." In the illustrated embodiment, for example, the electrode device 18 includes four openings 30 near the four corners of the open edge, and a suture 28 is passed through the four openings 30 and used to tie the edges together. In alternative embodiments, any other suitable closure mechanism may be used.

In general, the electrode devices 18, 20 of the system 10 are multipolar. In some embodiments, they may be bipolar, but typically they will include more than two electrodes. The number of electrodes may vary, for example, from as few as two to as many as twenty. It may be necessary or advantageous, however, to include as many electrodes as possible, while still keeping the electrode devices 18, 20 relatively small. In some embodiments, such as those described immediately below, the electrode devices 18, 20 may be hexapolar (six electrodes per device).

Figure 6:
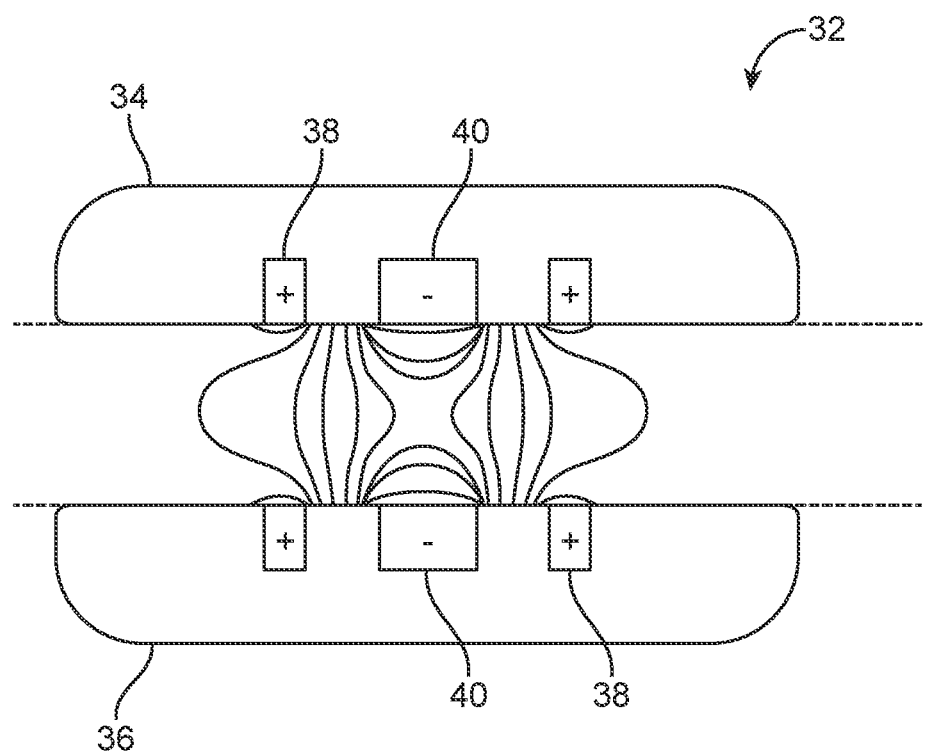
FIG. 6 is a cross-sectional/side view of a multipolar electrode of a system for stimulating a carotid sinus nerve, according to one embodiment.

With reference now to FIG. 6, a cross-sectional view of one embodiment of a multipolar electrode device 32 for use in the carotid nerve stimulation system 10 is illustrated. In this embodiment, the electrode device 32 includes an upper substrate 34, a lower substrate 36, four positively charged electrodes 38 and two negatively charged electrodes 40. In this embodiment, charge travels across the nerve between the electrodes 38, 40, between the two substrates 34, 36. Again, alternative embodiments may include any suitable number of electrodes and any suitable combinatorial arrangement of positive and negative electrodes.

Figure 7:
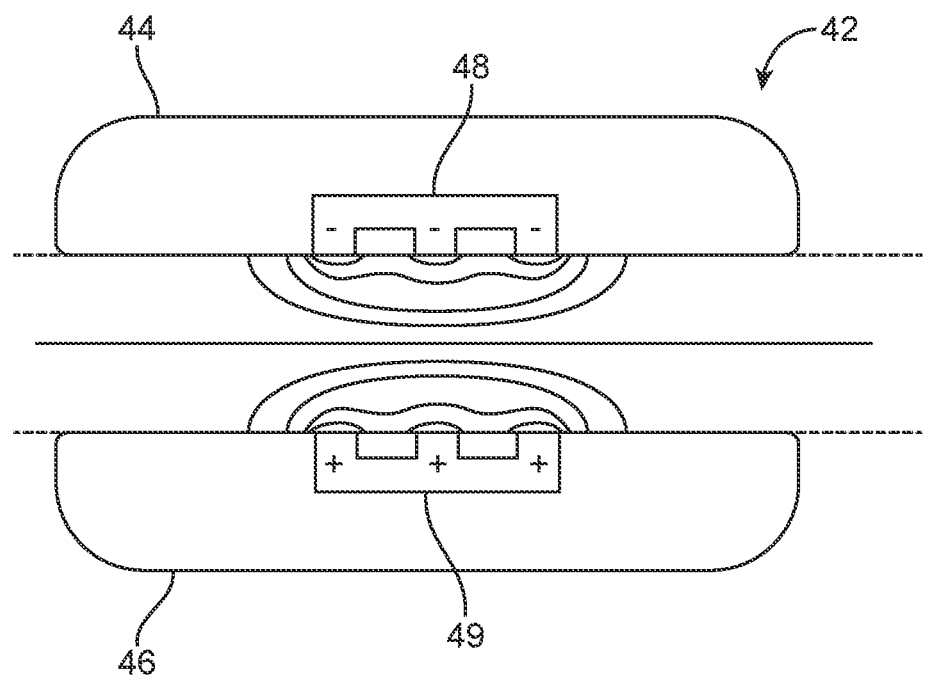
FIG. 7 is a cross-sectional/side view of a multipolar electrode of a system for stimulating a carotid sinus nerve, according to an alternative embodiment.

FIG. 7 is a cross-sectional view of an alternative embodiment of a multipolar electrode device 42 for use in the carotid nerve stimulation system 10. In this embodiment, the electrode device 42 also includes an upper substrate 34 and a lower substrate 36. The upper substrate 44 includes three negatively charged electrodes 48, and the lower substrate 46 includes three positively charged electrodes 49. In this embodiment, charge travels along the three negative electrodes 48 and along the positive electrodes 49, without traveling all the way across the nerve.

Figure 8:
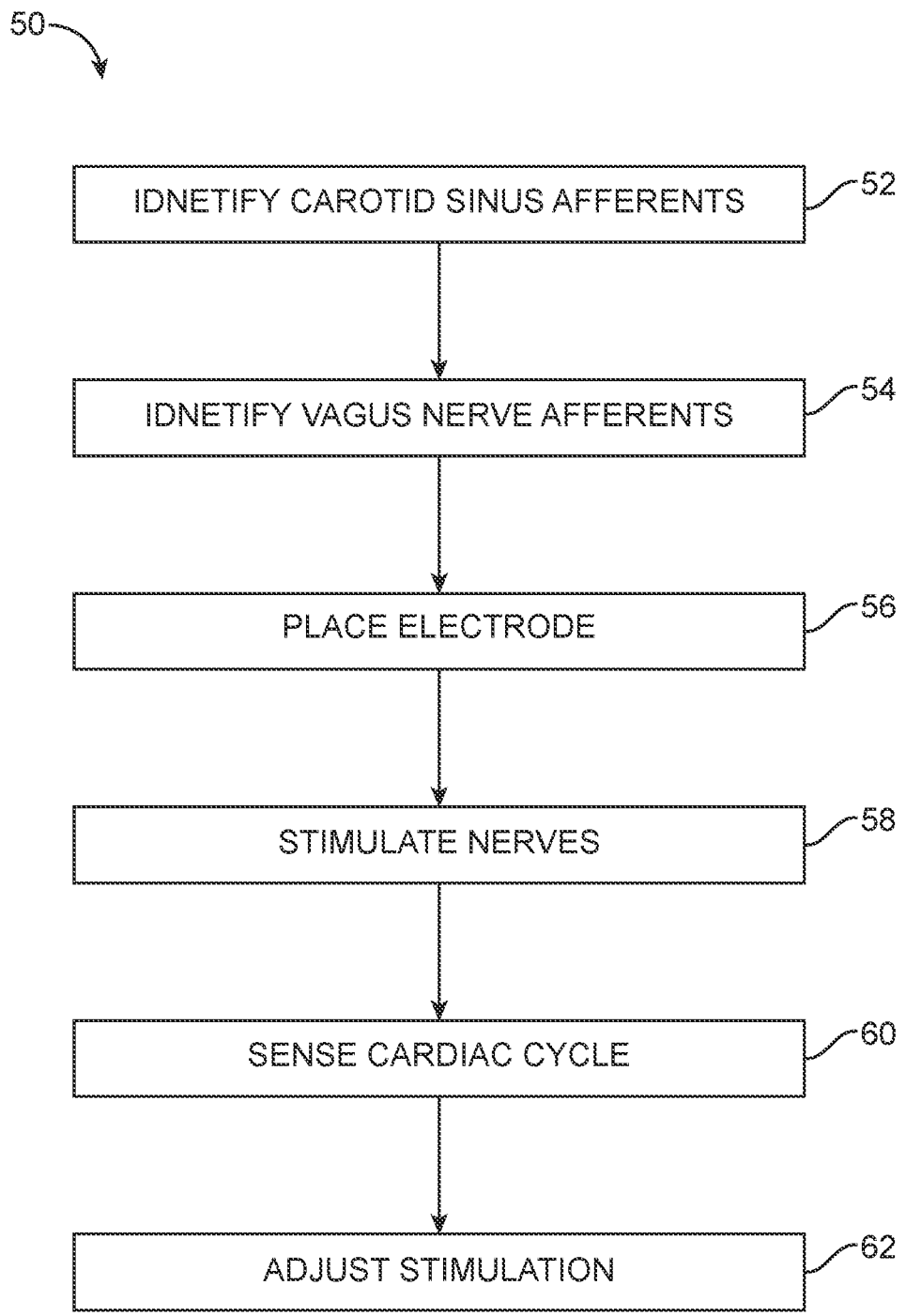
FIG. 8 is a flow chart illustrating a method for stimulating nerve fibers, according to one embodiment.

Referring now to FIG. 8, one embodiment of a method 50 for stimulating nerves to treat a condition is illustrated. In this embodiment, carotid sinus nerve afferent fibers and cardiac-specific vagus nerve afferent fibers are stimulated. In alternative embodiments, other combinations of nerves may be stimulated. As first steps, the method 50 involves identifying the carotid sinus afferent nerve fibers 52 and identifying the vagus nerve afferent fibers 54. These two steps 52, 54 are shown as separate boxes on FIG. 8, but in various embodiments they may be performed in the opposite order or simultaneously. In alternative embodiments, only one of the two steps 52, 54 may be performed.

Next an electrode device is placed 56 over the identified nerves. Then the nerves are stimulated 58, using the electrode. The patient's cardiac cycle may then be sensed 60 (or simply heart rate or other indicator), and the stimulation may then be adjusted 62, based on the sensed cardiac cycle. In one embodiment, for example, the stimulation frequency may be adjusted up or down, depending on the patient's heart rate. In alternative embodiments, any other suitable physiological parameters may be measured and used to adjust one or more stimulation parameters. For example, blood pressure may be measured by any suitable method, such office cuff, finger plethysmography, tonometery, or catheterization, and the measured pressure may then be used to adjust stimulation frequency and/or any other stimulation parameter. The cardiac sensing step 60 and the adjusting step 62 are optional, and in some embodiments one or both of them might not be performed. In some patients, both carotid sinus nerves and vagus nerves (in both sides of the neck) may be treated, in which case the steps of identifying 52, 54 and electrode placement 56 may be repeated for the second side of the neck, before the stimulation step 58. At least some of these steps are described in further detail immediately below.

Figure 9:
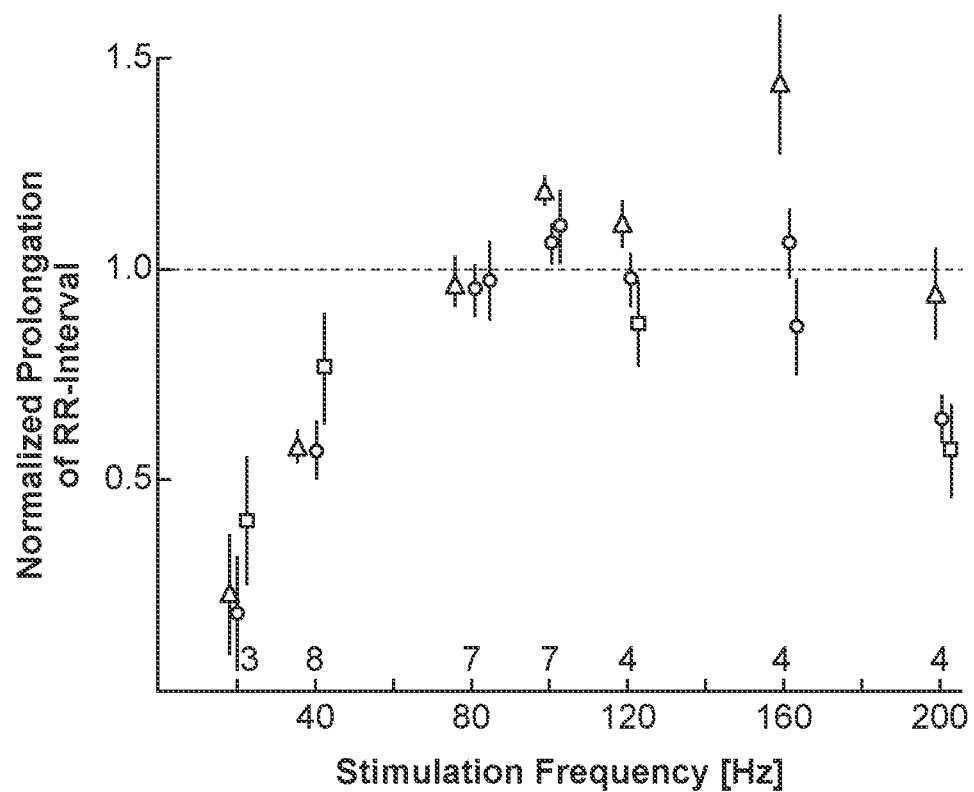
FIG. 9 is a chart illustrating prolongations of an R-R interval of the heart at different carotid sinus nerve stimulation frequencies, according to a prior art study.
Figure 10:
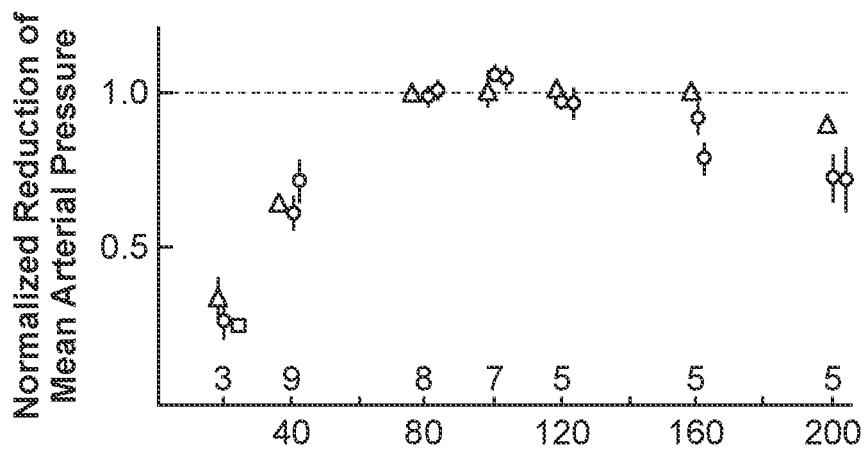
FIG. 10 is a chart illustrating reductions of mean arterial pressure at different carotid sinus nerve stimulation frequencies, according to a prior art study.
Figure 11:
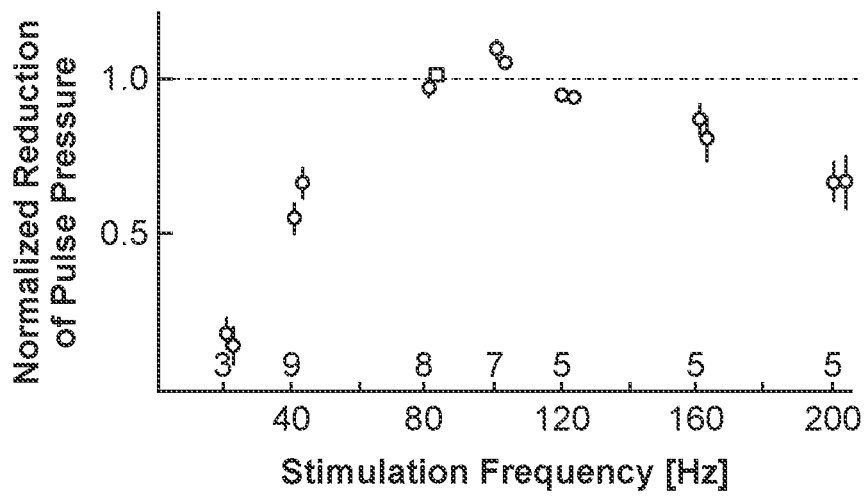
FIG. 11 is a chart illustrating reductions of pulse pressure at different carotid sinus nerve stimulation frequencies, according to a prior art study.

FIGS. 9-11 show results of a prior art study involving electrical stimulation of the carotid sinus nerve. (Borst, C. et. Al., Cardiovasc Res. 1974; 8(5):674-8). These studies described theoretically optimal stimulation frequencies to achieve maximal responses in heart rate (FIG. 9), arterial blood pressure (FIG. 10), and pulse pressure (FIG. 11). These study data show a plateau in the blood pressure and heart rate responses with stimulation frequencies of the carotid sinus nerve between 80-120 Hz, with a peaking of the response at 100 Hz. These responses were obtained in patients implanted with the Medtronic Baropacer™ or Angistat™ devices, which have limited programming parameters, namely fixed stimulation parameters for pulse widths and limited amplitude and frequency settings. These devices also employed bipolar stimulation electrodes and monophasic, square wave pulses.

Unlike the devices and methods used in the study highlighted in FIGS. 9-11, devices, systems and methods of the present application use hexapolar electrodes (or electrode devices with even more electrodes/poles), allowing for multiple electrode configuration. The system also includes the programmable pulse generator 12, with charge balanced stimulation waveforms and stimulation parameters ranging from 1-25 mA amplitude, 0.06-5 ms pulse widths and 1-5000 Hz frequency. Any or all of the three parameters—amplitude, pulse width and frequency—may be adjusted for any given patient.

Optimal responses may be defined as peak drop in blood pressure, heart rate, augmentation index, wave reflection coefficient or peak increases in cardiac output, subendocardial viability ratio (SEVR), or any combination thereof, measured for example at follow-up post-implant. In some embodiments, the nerve stimulation system 10 may be used to adjust the frequency of stimulation, such that the number of electrical impulses delivered is constant per cardiac cycle, scaled to the instantaneous heart rate. Calibration of the stimulation may provided by a sensor, such as the ECG sensor 24, a blood pressure waveform, phonocardiography, arterial distension waveform, and/or the like.

Figure 12A:
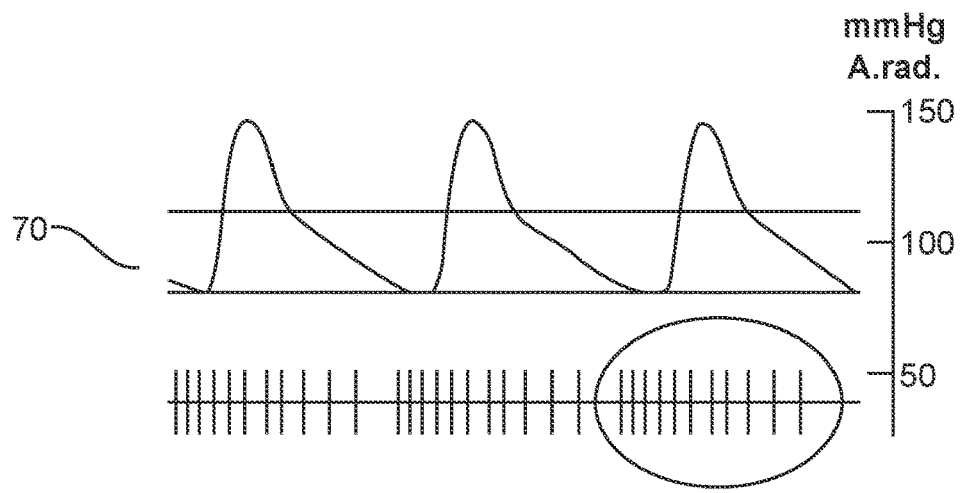
FIGS. 12A-C are a set of three charts comparing three different timings of baroreceptor stimulation, relative to an electrocardiogram tracing of a heart rhythm.
Figure 12B:
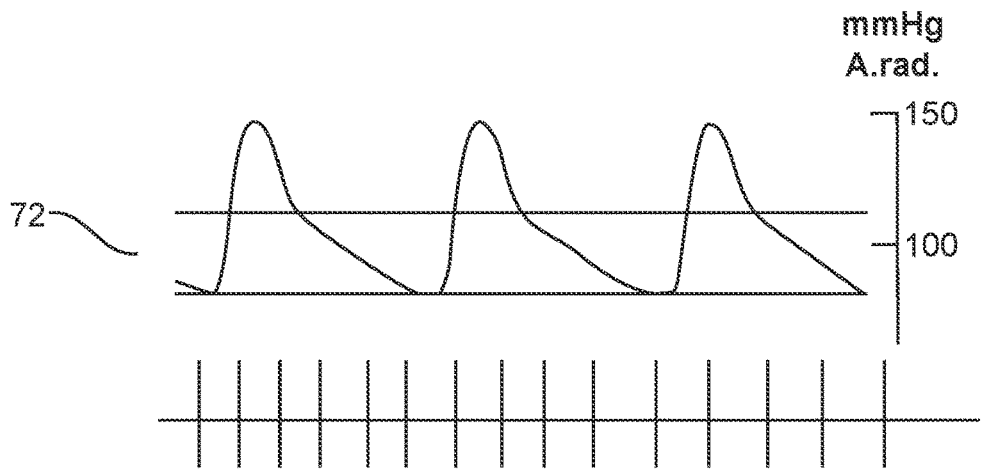
Figure 12C:
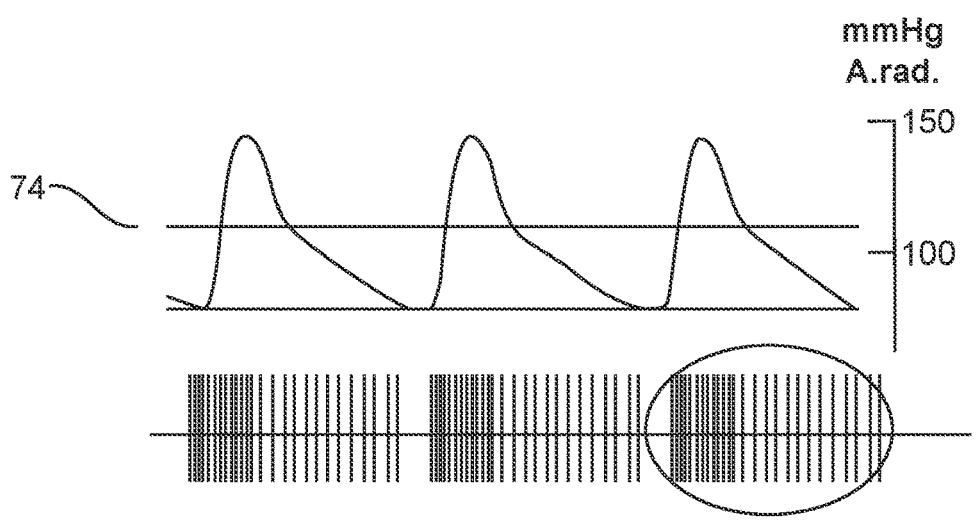

FIG. 12 contrasts a stimulation method according to one embodiment of the present application to a stimulation method of a prior art device. The top panel shows physiologic (natural) stimulation of the baroreceptors. The middle panel shows a prior art method of constant frequency stimulation, where the baroreceptors are stimulated at the same frequency regardless of the patient's heart rate. The bottom panel shows one embodiment of the methods described in this application, in which a closed loop is created. In this embodiment, the frequency of stimulations of the carotid sinus nerve and vagus nerve is adjusted according to the patient's heart rate, which is shown here as the ECG tracing of the patient's cardiac cycle. The stimulations need not be timed to the cardiac cycle, as shown here, but the frequency is simply adjusted based on the heart rate. In some embodiments, instantaneous frequency of stimulation may also be adjusted, as shown in the bottom panel of FIG. 12, such that 25% of the pulse train is delivered at the onset of the sensed signal corresponding to the systolic phase and the remainder delivered during the diastolic phase.

In one example of a nerve stimulation method, the implantable portion of the nerve stimulation system 10 may first be implanted in the patient. This portion includes all components of the system 10, other than the computing device 26. The implantable portion of the system 10 may be tested and/or calibrated during implantation. At initial implantation, the system 10 may be turned off or turned on with a given set of stimulation parameters. After implantation, a healthcare provider (physician, physician's assistant, nurse, medical technician, etc.) may meet with the patient and test the stimulation system 10, for example by instructing the pulse generator 12 to stimulate the carotid sinus nerve and vagus nerve for a period of time. In some cases, this may be performed while the patient is engaging in different levels of activity, such as sitting, standing, walking or the like. The healthcare provider may then use the computing device 26 to adjust one or more of the parameters, for example the stimulation frequency, based on the patient's physiological reaction to stimulation and different activity levels. Different patients, for example, may respond differently to different stimulation frequencies, such as but not limited to within the range of 80-120 Hz. The patient may return periodically to the healthcare provider for checkups and adjustments, as needed.

The above description is intended to be a complete description exemplary embodiments and features of a method, device and system for stimulating carotid sinus nerves to treat drug resistant hypertension and/or other conditions. It is meant to be a description of examples only and is not intended to limit the scope of the invention.

We claim:

1. A method for stimulating nerve fibers to treat a condition in a patient, the method comprising:
   identifying carotid sinus nerve afferent fibers in a first side of a patient's neck;
   identifying cardiac-specific vagal nerve afferent fibers in the first side of the patient's neck;
   placing a first multipolar electrode device around the carotid sinus nerve afferent fibers and the cardiac-specific vagal nerve afferent fibers;
   stimulating the carotid sinus nerve afferent fibers and the cardiac-specific vagal nerve afferent fibers, using the first multipolar electrode device;
   sensing a heart rate of the patient; and
   timing the stimulation of the carotid sinus nerve afferent fibers and the cardiac-specific vagal nerve afferent fibers to the sensed heart rate, wherein timing the stimulation comprises:
      delivering 25 percent of a pulse train of the stimulation at the onset of a sensed signal corresponding to a systolic phase of the patient's heartbeat; and
      delivering a remaining 75 percent of the pulse train during a diastolic phase of the patient's heartbeat.

2. The method of claim 1, wherein stimulating the carotid sinus nerve afferent fibers and the cardiac-specific vagal nerve afferent fibers comprises sending a stimulation signal from a pulse generator implanted in the patient through a first lead to the first multipolar electrode device.

3. The method of claim 1, wherein identifying the carotid sinus nerve afferent fibers comprises identifying a nerve plexus near the carotid sinus.

4. The method of claim 1, further comprising:
   identifying carotid sinus nerve afferent fibers in a second side of the patient's neck;
   identifying cardiac-specific vagal nerve afferent fibers in the second side of the patient's neck;

placing a second multipolar electrode device around the carotid sinus nerve afferent fibers and the cardiac-specific vagal nerve afferent fibers in the second side; and stimulating the carotid sinus nerve afferent fibers and the cardiac-specific vagal nerve afferent fibers in the second side, using the second multipolar electrode device.

5. The method of claim 4, wherein stimulating the carotid sinus nerve afferent fibers and the cardiac-specific vagal nerve afferent fibers comprises:

sending a first stimulation signal from a pulse generator implanted in the patient through a first lead to the first multipolar electrode device; and sending a second stimulation signal from a pulse generator implanted in the patient through a second lead to the second multipolar electrode device.

6. The method of claim 1, wherein the multipolar electrode device is a hexapolar electrode.

7. The method of claim 1, wherein stimulating the carotid sinus nerve afferent fibers and the cardiac-specific vagal nerve afferent fibers comprises providing a stimulation signal with parameters in the ranges of 1-25 mA amplitude, 0.06-5 ms pulse widths and 1-5000 Hz frequency.

8. The method of claim 7, wherein stimulation is at a frequency of between 80 Hz and 120 Hz.

9. The method of claim 8, wherein timing the stimulation comprises adjusting a frequency of the stimulation such that a number of delivered electrical impulses is constant for each cardiac cycle of the patient's heart.

10. The method of claim 8, wherein sensing the heart rate comprises using data selected from the group consisting of an electrocardiogram, a blood pressure waveform, a phonocardiograph and an arterial distension waveform.

11. The method of claim 8, wherein timing the stimulation comprises delivering all of a pulse train of the stimulation during a diastolic phase of the patient's heartbeat.

12. The method of claim 1, wherein stimulating the carotid sinus nerve afferent fibers and the cardiac-specific vagal nerve afferent fibers comprises selectively stimulating only afferent nerve fibers and not stimulating efferent nerve fibers.

13. An implantable system for stimulating nerve fibers to treat a condition in a patient, the system comprising:

a pulse generator;

a first multipolar electrode device configured to wrap around carotid sinus nerve afferent fibers and cardiac-specific vagal nerve afferent fibers in a first side of a patient's neck;

a first lead attached at one end to the pulse generator and at an opposite end to the first multipolar electrode device; and a computing device wirelessly connected to the pulse generator and configured to receive a sensed heart rate from an electrocardiogram sensor and transmit at least one stimulation parameter to the pulse generator, wherein the computing device is configured to time a stimulation of the carotid sinus nerve afferent fibers and the cardiac-specific vagal nerve afferent fibers to the sensed heart rate, wherein timing the stimulation comprises:

delivering 25 percent of a pulse train of the stimulation at the onset of a sensed signal corresponding to a systolic phase of the patient's heartbeat; and delivering a remaining 75 percent of the pulse train during a diastolic phase of the patient's heartbeat.

14. The system of claim 13, wherein the first multipolar electrode device is a hexapolar electrode.

15. The system of claim 14, wherein the first multipolar electrode device is flexible and has two flaps connected along one edge and open along an opposite edge, wherein the open opposite edge is configured to admit the carotid sinus nerve afferent fibers and cardiac-specific vagal nerve afferent fibers.

16. The system of claim 13, further comprising:

a second multipolar electrode device configured to wrap around carotid sinus nerve afferent fibers and cardiac-specific vagal nerve afferent fibers in a second side of the patient's neck; and a second lead attached at one end to the pulse generator and at an opposite end to the second multipolar electrode device.

17. The system of claim 16, wherein the system comprises the electrocardiogram sensor, the system further comprising:

a third lead attached at one end to the pulse generator and at an opposite end to the electrocardiogram sensor.

18. The system of claim 17, wherein the electrocardiogram sensor comprises:

a paddle-shaped substrate; and multiple electrodes positioned along the paddle-shaped substrate.

19. The system of claim 13, wherein the first multipolar electrode device is configured to selectively stimulate the carotid sinus nerve afferent fibers and the cardiac-specific vagal nerve afferent fibers and to not stimulate efferent nerve fibers.

\* \* \* \* \*